United States Patent [19]

Scheibel et al.

[11] Patent Number: 5,334,764
[45] Date of Patent: Aug. 2, 1994

[54] PROCESS FOR PREPARING N-ALKAYL POLYHYDROXY AMINES

[75] Inventors: Jeffrey J. Scheibel; Daniel S. Connor; Robert E. Shumate; James B. St. Laurent, all of Cincinnati, Ohio

[73] Assignee: The Procter & Gamble Company, Cincinnati, Ohio

[21] Appl. No.: 59,000

[22] Filed: May 6, 1993

Related U.S. Application Data

[60] Division of Ser. No. 938,576, Aug. 31, 1992, abandoned, which is a continuation of Ser. No. 598,462, Oct. 12, 1990, abandoned.

[51] Int. Cl.$^5$ ............................................ B07C 209/00
[52] U.S. Cl. ..................... 564/487; 564/469; 564/489
[58] Field of Search ............... 564/471, 487, 489, 469; 554/65, 68; 252/548

[56] References Cited

U.S. PATENT DOCUMENTS 2,016,962 10/1935 Flint et al. ........................... 564/471

FOREIGN PATENT DOCUMENTS 519381 3/1940 United Kingdom ............... 564/471

*Primary Examiner*—José G. Dees
*Assistant Examiner*—Deborah D. Carr
*Attorney, Agent, or Firm*—Jerry J. Yetter; George W. Allen

[57] ABSTRACT

Amines such as methyl amine are reacted with materials such as reducing sugars in hydroxy solvents such as methanol to prepare N-alkyl polyhydroxy amines. Accordingly, glucose is reacted with methyl amine and the resulting adduct is hydrogenated to yield N-methylglucamine. The N-alkyl polyhydroxyamines can be subsequently reacted with fatty esters to provide polyhydroxy fatty acid amides useful as detersive surfactants. Thus, detersive surfactants are available from non-petrochemical precursors such as sugars and sugar sources such as corn syrup, and fatty acid esters derivable from various fats and oils.

1 Claim, No Drawings

PROCESS FOR PREPARING N-ALKAYL POLYHYDROXY AMINES

This is a division of application Ser. No. 07/938,576, filed on Aug. 31, 1992, which is a continuation of application Ser. No. 07/598,462, filed on Oct. 12, 1990, now abandoned.

FIELD OF THE INVENTION

The present invention relates to a chemical process for preparing N-alkyl polyhydroxy amines, especially N-methylglucamine, as well as fatty acid amide derivatives thereof useful as detersive surfactants.

BACKGROUND OF THE INVENTION

The manufacture of N-alkyl polyhydroxy amines, such as N-methylglucamine, has been known for many years, and such materials are available commercially. In the main, however, their use has been somewhat limited and such materials have been relatively expensive. Recently, there has been occasion to employ N-alkyl polyhydroxy amines in reactions with fatty acid esters to prepare fatty acid polyhydroxy amide detersive surfactants for use in cleaning products. As can be imagined, were the cost of N-alkyl polyhydroxy amines to remain high, this laundry detergent use of the fatty acid polyhydroxy amide surfactants would be impossible. Accordingly, there is a continuing search for quick, inexpensive means for preparing N-alkyl polyhydroxy amines on a commercial scale.

Moreover, it is has been determined that care must be taken in preparing N-alkyl polyhydroxy amines in a form that is suitable for subsequent reaction with fatty acid methyl esters, since contamination of the N-alkyl polyhydroxy amines with, for example, hydrogenation catalysts such as Raney nickel, unreacted sugars, water, and the like, can seriously impact on the formation of the fatty acid polyhydroxy amide formation. For example, browning reactions, with the formation of undesirable color bodies, can occur. The formation of various undesirable by-products such as cyclic materials and/or ester-amides can also occur. In a worse case scenario, by-product formation can be so high that the desired reaction of the N-alkyl polyhydroxy amine with the fatty acid methyl ester is essentially stopped in its entirety, with the formation of black, intractable tarry products.

The present invention provides a simple means for preparing N-alkyl polyhydroxy amines, especially N-methylglucamine, in high yields, with low color formation, and in a form that is particularly suited for subsequent reaction with fatty acid esters.

BACKGROUND ART

A number of years ago, processes were explored for making textile assistants or detergents from fatty acids or their derivatives in combination with N-alkylglucamines, the latter made by reductive amination of glucose. Glucose reductive amination processes are more fully disclosed in U.S. Pat. No. 2,016,962, Flint et al, issued Oct. 8, 1935.

U.S. Pat. No. 1,985,424, Piggott, issued Dec. 25, 1934 discloses manufacturing "textile assistants" by reacting (a) the product of heating glucose and aqueous methylamine in presence of hydrogen and a hydrogenating catalyst under pressure with (b) an organic carboxylic acid such as stearic acid or oleic acid. The condensation product, prepared at about 160° C., is said to be "predominantly, if not exclusively, an amide" and is assertedly of the formula R—CO—NR$_1$—CH$_2$—(CHOH)$_4$—CH$_2$OH wherein R is an alkyl radical containing at least 3 carbon atoms, while R$_1$ is hydrogen or an alkyl radical.

U.S. Pat. No. 2,703,798, Schwartz, issued Mar. 8, 1955 asserts that compositions produced by reacting fatty acids or acid anhydrides with N-alkylglucamines (presumably such as the process as taught by Piggott) have poor color and poor detergency properties. It is indeed chemically reasonable that more than one compound can be formed by the Piggott process. Piggott makes no attempt to quantitatively prove the structures of the compounds or mixtures he prepared.

Schwartz ('798) goes on to report an improvement as a result of reacting fatty ester (as distinct from fatty acid or anhydride) with N-alkylglucamines. Although this process may overcome one or another deficiency of the art, such as of Piggott, it now transpires that the Schwartz process still has difficulties, in particular, in that complex mixtures of compounds can be formed even by the Schwartz process. The reaction may take several hours and the process can fail to give high quality product. Neither the process of Piggott not the process of Schwartz is known to have ever borne fruit in commercial practice.

In more detail, Schwartz notes that only one of several possible chemical reactions takes place when N-monoalkylglucamines are condensed with fatty esters or oils. The reaction is said to give compounds formulated as amides, e.g.,

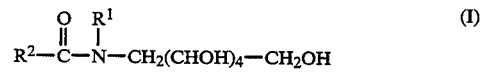

$$R^2-\underset{\underset{O}{\|}}{C}-\underset{\underset{R^1}{|}}{N}-CH_2(CHOH)_4-CH_2OH \qquad (I)$$

where R$^2$ is fatty alkyl and R$^1$ is a short-chain alkyl, typically methyl. This structure is apparently the same as the structure proposed by Piggott. Schwartz contrasts the single-product outcome he believes he secures with compounds he asserts are actually produced when acids are reacted with N-alkylglucamines, namely mixtures of the amide (I) with one or more by-products, to which he assigns esteramide and esteramine structures and which assertedly include compounds which are "inert and waxy, impairing the surface activity of" the structure (I) amide.

According to Schwartz, approximately equimolar proportions of N-monoalkylglucamines can be reacted with fatty alkyl esters by heating at 140° C.-230° C., preferably 160° C.-180° C. at normal, reduced or superatmospheric pressures for a period "somewhat in excess of one hour" during which time two initially immiscible phases merge to form a product said to be a useful detergent.

Suitable N-monoalkylglucamines are illustrated by N-methylglucamine, N-ethylglucamine, N-isopropylglucamine and N-butylglucamine. Suitable fatty alkyl esters are illustrated by the product of reacting a C$_6$-C$_{30}$ fatty acid with an aliphatic alcohol e.g., methyl ester of lauric acid. Mixed glycerides of Manila oil or mixed glycerides of cochin coconut oil can apparently also be used as the fatty ester. When the glucamine is N-methylglucamine, the corresponding products with these fatty esters are characterized as the "fatty acid amides of N-methylglucamine", which are useful detergent surfactants. Another specific composition reported is assertedly "N-isopropylglucamine coconut fatty acid amide".

U.S. Pat. No. 2,993,887, Zech, issued Jul. 25, 1961 reveals there is even more complexity to the reactions of fatty substances with N-methylglucamine. In particular, Zech asserts that the products of high-temperature reaction (180° C.-200° C.) within the range disclosed by Schwartz have cyclic structures. No fewer than four possible structures are given. See '887 at column 1, line 63 - column 2, line 31.

What is now believed actually to be provided by the fatty ester- N-alkylglucamine process of Schwartz are compositions comprising mixtures of formula (I) compounds together with appreciable proportions (e.g., about 25%, often much more) of several other components, especially cyclic glucamide by-products (including but not limited to the structures proposed by Zech) or related derivatives such as esteramides wherein as compared with formula (I) at least one -OH moiety is esterified.

Moreover, a reinvestigation of Schwartz suggests that there are other significant unsolved problems in the process, including a tendency to form trace materials imparting very unsatisfactory color and/or odor to the product.

More recently, the work of Schwartz notwithstanding, Hildreth has asserted that compounds of formula (I) are new. See Biochem. J., 1982, Vol. 207, pages 363-366. In any event, these compositions are given a new name: "N-D-gluco-N-methylalkanamide detergents", and the acronym "MEGA". Hildreth provides a solvent-assisted process for making the compounds differing seminally from Schwartz in that it returns to the use of a fatty acid reactant, instead of fatty ester. Moreover, Hildreth relies on pyridine/ethyl chloroformate as the solvent/activator. This process is specifically illustrated for octanoyl-N-methylglucamide ("OMEGA"), nonanoyl-N-methylglucamide ("MEGA-9") and decanoyl-N-methylglucamide ("MEGA-10"). The process is said to be cheap and high-yield. One must of course assume that "cheap" is relative and is meant in the sense of specialized biochemical applications of interest to the author: in terms of large-scale detergent manufacture, the use of pyridine and ethyl chloroformate would hardly be viewed as consistent with an economic or environmentally attractive process. Therefore, the Hildreth process is not further considered herein.

Hildreth and other workers have purified certain formula (I) compounds, e.g., by recrystallization, and have described the properties of some of the structure (I) compounds. Recrystallization is, of course, a costly and potentially hazardous (flammable solvents) step in itself, and large-scale detergent manufacture would be more economical and safer without it.

According to Schwartz supra, the products of the Schwartz process can be used for cleaning hard surfaces. According to Thomas Hedley & Co. Ltd. (now Procter & Gamble), British Patent 809,060 published Feb. 18, 1959, formula (I) compounds are useful as a surfactant for laundry detergents such as those having granular form. Hildreth (supra) mentions use of compounds of formula (I) in the biochemistry field as a detergent agent for solubilizing plasma membranes and EP-A 285,768, published Dec. 10, 1988 describes application of formula (I) compounds as a thickener. Thus, these compounds, or compositions containing them, can be highly desirable surfactants.

Yet another process for making compositions comprising formula (I) compounds is included in the above-identified disclosure of improved thickeners. See EP-A 285,768. See also H. Kelkenberg, Tenside Surfactants Detergents 25 (1988) 8-13, inter alia for additional disclosures of processes for making N-alkylglucamines which, along with the above-identified art-disclosed N-alkylglucamine processes can be combined with the instant process for an overall conversion of glucose and fatty materials to useful surfactant compositions.

The relevant disclosures of EP-A 285,768 include a brief statement to the effect that "it is known that the preparation of chemical compounds of formula (I) is done by reacting fatty acids or fatty acid esters in a melt with polyhydroxy alkylamines which can be N-substituted, optionally in the presence of alkaline catalysts". The above-referenced art strongly suggests that this statement is a gross simplification or is inaccurate. EP-A 285,768 does not cite any references in support of the quoted statement, nor has any reference other than EP-A 285,768 been found which actually does disclose any catalytic condensation of N-alkylglucamines with fatty esters or fatty triglycerides.

The European Patent Application contains the following Example entitled "Preparation of N-methyl-coconut fatty acid glucamide" in which "Na methylate" is understood to be synonymous with "sodium methoxide" and which has been translated from the German:

In a stirred flask 669 g (3.0 mol) of coconut fatty acid methyl ester and 585 g (3.0 mol) of N-methyl glucamine with the addition of 3.3 g Na methylate were gradually heated to 135° C. The methanol formed during the reaction was condensed under increasing vacuum at 100 to 15 mbar in a cooled collector. After the methanol evolution ended the reaction mixture was dissolved in 1.5 l of warm isopropanol, filtered and crystallized. After filtration and drying 882 g (:76% of theoretical) of waxy N-methyl coconut fatty acid glucamide was obtained. Softening point: 80° to 84° C.; Base number: 4 mg. KOH/g.

EP-A 285,768 continues with the following:

"In a similar manner the following fatty acid glucamides were prepared:

|  | Yield % | Softening Point (°C.) | Base No. (mg. KOH/g) |
|---|---|---|---|
| N-methyl lauric acid glucamide | 76 | 94-96 | 6 |
| N-methyl myristic acid glucamide | 75 | 98-100 | 3 |
| N-methyl palmitic acid glucamide | 75 | 103-105 | 5 |
| N-methyl stearic acid glucamide | 84 | 96-98 | 6" |

To summarize some important points of what can be gleaned from the art, the aforementioned Schwartz patent teaches that the problem of making formula (I) compounds from fatty esters or triglycerides and an N-alkylglucamine is solved by selecting fatty ester (instead of fatty acid) as the fatty reactant, and by doing simple uncatalyzed condensations. Later literature, such as Hildreth, changes direction back to a fatty acid-type synthesis, but does not document either that the teaching of the Schwartz patent is in error or how, short of making highly pure formula (I) compounds, to make such surfactants to detergent formulator's specifications. On the other hand, there has been one disclosure, in a totally different technical field, of sodium methoxidecatalyzed formula (I) compound synthesis. As noted,

SUMMARY OF THE INVENTION

The present invention encompasses a process (carried out under non-oxidizing conditions) for preparing N-alkyl polyhydroxy amines, comprising the steps of:

a) reacting a reducing sugar or reducing sugar derivative with a primary amine at mole ratios of amine:-sugar not greater than about 7:1 in an organic hydroxy solvent to provide an adduct;

b) reacting said adduct from step (a) with hydrogen under mild conditions, said adduct being substantially free from unreacted amine starting material, and said adduct being dissolved in said solvent, in the presence of a catalyst; and c) removing said catalyst and substantially removing the water in the reaction mixture to secure the N-alkyl polyhydroxy amine.

A preferred process herein is wherein the sugar material is a reducing sugar, especially glucose, and the amine compound is a member selected from the group consisting of $C_1$-$C_4$ alkyl or hydroxyalkyl amines. When the amine is monomethyl amine (hereinafter, simply "methyl amine") and the sugar is glucose, the preferred reaction product N-methylglucamine is secured. A particular advantage of the present process is that it can be carried out in the presence of water in step (a). Accordingly, raw materials such as corn syrup, and the like, can be used as the sugar source.

The catalyst used in step (b) is preferably a particulate nickel catalyst. Raney nickel can be used, but nickel affixed to substrate materials such as silica or alumina is preferred, since such substrate/metal catalysts are easier to remove (e.g., by filtration) in step (c) of the process.

Step (a) of the process is preferably carried out at a temperature of from about 0° C. to about 80° C., preferably from about 30° C. to about 60° C. Step (b) of the process is preferably carried out at a temperature of from about 40° C. to about 120° C., preferably from about 50° C. to about 90° C. Steps (a) and (b) of the R-1 process are preferably conducted under non-oxidizing conditions (e.g., inert gas) to provide good color. Catalyst removal is, of course, done under inert conditions due to fire hazard.

The invention herein also encompasses an overall process for preparing polyhydroxy fatty acid amide surfactants which includes an amide-forming reaction comprising reacting the N-alkyl polyhydroxy amine materials prepared in the foregoing manner with fatty acid esters in an organic hydroxy solvent in the presence of a base catalyst. The formation of such surfactants with high purity and low color is an especially beneficial result of the present process, since it allows the detergent formulator to pump or otherwise incorporate the polyhydroxy fatty acid amide reaction product plus the reaction solvent such as 1,2-propylene glycol, glycerol, or alcohol (e.g., in liquid detergents) directly into the final detergent formulation. This offers economic advantages in that a final solvent removal step is rendered unnecessary, particularly where glycols or ethanol is used.

All percentages, ratios and proportions herein are by weight, unless otherwise specified.

DETAILED DESCRIPTION OF THE INVENTION

The reaction for the preparation of the polyhydroxyamines herein can be termed the "R-1" reaction, and is illustrated by the formation of N-methylglucamine, wherein $R^1$ is methyl.

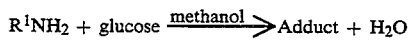

The reactants, solvents and catalysts used in the R-1 reaction are all well-known materials which are routinely available from a variety of commercial sources. The following are nonlimiting examples of materials which can be used herein.

Amine Material—The amines useful in the R-1 reaction herein are primary amines of the formula $R^1NH_2$, wherein $R^1$ is, for example, alkyl, especially $C_1$-$C_4$ alkyl, or $C_1$-$C_4$ hydroxyalkyl. Examples include methyl, ethyl, propyl, hydroxyethyl, and the like. Nonlimiting examples of amines useful herein include methyl amine, ethyl amine, propyl amine, butyl amine, 2-hydroxypropyl amine, 2-hydroxyethyl amine; methyl amine is preferred. All such amines are jointly referred to herein as "N-alkyl amines".

Polyhydroxy Material—A preferred source of polyhydroxy materials useful in the R-1 reaction comprises reducing sugars or reducing sugar derivatives. More specifically, reducing sugars useful herein include glucose (preferred), maltose, fructose, maltotriose, xylose, galactose, lactose, and mixtures thereof.

Catalyst—A variety of hydrogenation catalysts can be used in the R-1 reaction. Included among such catalysts are nickel (preferred), platinum, palladium, iron, cobalt, tungsten, various hydrogenation alloys, and the like. A highly preferred catalyst herein comprises "United Catalyst G49B" a particulate Ni catalyst supported on silica, available from United Catalysts, Inc., Louisville, Ky.

Solvent—Formation of the adduct in the R-1 process is conveniently carried out in an organic solvent, especially polar, most preferably hydroxy solvents. Typical examples of solvents useful herein in the formation of the amine-sugar adduct include methanol (preferred), ethanol, 1-propanol, iso-propanol, the butanols, ethylene glycol, 1,2-propylene glycol, 1,3-propylene glycol, glycerol and the like.

The hydrogenation reaction of the R-1 reaction is also carried out in the presence of an organic solvent which dissolves the adduct. Hydrogenation solvents are, conveniently, polar, especially hydroxy, solvents, i.e., of the same type as those mentioned above for use in the formation of the adduct. Methanol is a preferred solvent for use in the hydrogenation reaction.

General R-1 Reaction Conditions—Reaction conditions for the R-1 reaction are as follows.

(a) Adduct formation - The reaction time used for adduct formation will typically be on the order of 0.5-20 hours, depending somewhat on the reaction temperature chosen. In general, lower reaction temperatures in the range of 0° C.-80° C. require longer reaction times, and vice-versa. In general, over the preferred 30° C.-60° C. reaction temperature range, good adduct yields are achieved in 1-10 hours. Reactant concentrations can vary. Molar ratios of amine:sugar not greater than about 7:1 are used herein. Generally good adduct formation is achieved at about a 1:1 mole ratio of amine:sugar; some slight excess of amine is preferably used, e.g., mole ratios of 1.05:1; 1.1:1; 2:1, and the like. Typical reactant concentrations in the hydroxy solvent are in the 10%-60% (wt.) range. Adduct formation can be carried out at atmospheric or superatmospheric pressures.

(b) Reaction with Hydrogen—The reaction with hydrogen is preferably carried out with limited initial water, although water (e.g., up to 1:1 wt. $H_2O$:alcohol) can be present. Optional water removal from the adduct prepared in step (a) can be effected by use of drying agents, or by simply stripping water and solvent from the adduct, and then redissolving the adduct in fresh water-free solvent. The hydrogen reaction can typically be run, for example, at temperatures of 40° C.–120° C. at 50–1,000 psi or, for example, at 50° C.–90° C. at 100–500 psi for periods of 0.1–35 hours, generally 0.5–8 hours, typically 1–3 hours. The adduct/solvent solution used in the hydrogen reaction is typically at a 10%-60% (wt.) solute level. (It will be appreciated that the selection of hydrogen reaction conditions will depend somewhat on the type of pressure equipment available to the formulator, so the above-noted reaction conditions can be varied without departing from this invention.) Hydrogen reaction catalyst levels are typically 1% to 100%, preferably about 2% to about 20% solids weight, calculated based on wt. catalyst:wt. reducing sugar substituent. The product of step (b) is dried by solvent/water stripping, or by crystallization or by means of effective drying agents. This helps prevent reversion to the sugar starting material.

With regard to step (b) involving reaction of the adduct from step (a) with hydrogen, it is preferred that the adduct be substantially free from interfering amounts of unreacted amine starting material. While not intending to be limited by theory, it appears that such amines can undesirably affect the reaction with hydrogen, perhaps by modifying the surface of the metal catalyst, especially the preferred substrate-supported metal catalysts used herein. Whatever the mechanism, it is preferred that levels of unreacted amine be kept low, although a few percent (e.g., below about 20 weight percent of the adduct) can be present, assuming the formulator is willing to adjust levels of metal catalyst according to need. In any event, removal of unreacted amine to provide the adduct in a form substantially free from interfering amounts of unreacted amine prior to the reaction with hydrogen is a straightforward matter, especially with volatile amines such as methyl amine. Thus, vacuum or heat stripping of the amine can be employed. Indeed, in the Examples hereinafter the unreacted amine is automatically removed when the solvent and water are stripped from the adduct prior to the reaction with hydrogen. Or, the reaction stoichiometry can be such that the amount of residual, unreacted amine is of little consequence to the subsequent hydrogen reaction step.

EXAMPLE I

A typical R-1 reaction is as follows. A reaction mixture comprising methyl amine (10.73 g.; 40% solution in $H_2O$; Aldrich), glucose (25 g.) and ethanol (100 mls.) is prepared at room temperature, allowed to stand overnight and is boiled away at 40° C. on a rotary evaporator to provide a solid adduct. 21.56 g. of the adduct are admixed with 110 mls methanol and 2 g. of United Catalyst G49B in a rocking autoclave and hydrogenated at 50° C. for 28 hours at about 250 psi hydrogen. The reaction product is then removed from the rocking autoclave and hot filtered through a glass microfibre filter (Whatman, 934-AH) to remove nickel. (A slight yellowish/greenish tinge to the solution/product can indicate the presence of trace amounts of nickel: final traces of nickel can be removed by, for example, filtration through neutral silica gel or bleaching earth). The N-methylglucamine can be recovered as a substantially white solid, e.g., by evaporating the methanol, preferably with reduced heat (below 60° C.) under vacuum. The product is in a form suitable for any desired use; it is particularly suitable for reaction with fatty acid esters to provide fatty acid polyhydroxy amides.

EXAMPLE II

An R-1 reaction using corn syrup as a reactant is as follows.

Corn syrup (28.75 g., 71% in water, 99% glucose composition, Cargill ), 75 mls. of methanol (anhydrous) and 2.0 g. of Ni catalyst (G49B, United Catalyst) are charged to an autoclave glass liner. The glass liner is placed into the rocking autoclave. The reaction mixture is purged twice with 200 psig $N_2$ and once with 200 psig $H_2$. Next, the reaction mixture is charged with 250–259 psig $H_2$ and the reaction heated to 60° C. for 1 hour. Methylamine (28 mls.; 8.03 molar in ethanol; Fluka Chemicals) is charged to the reactor under pressure. The reaction is continued for 7 hours at 60° C. then cooled to room temperature. At room temperature, the reaction solidifies in the reactor and the filtrate is removed directly from the reactor (which contains an internal filter) under pressure. The catalyst thus remains in the reactor. The filtrate is colorless and is dried down to give 2.91 grams of product. The reactor is charged with methanol (50 mls.) and heated to 60° C. for 2 hours, at which time the first wash is recovered. Another 50 mls. methanol is added to reactor and heated at 70° C. for 30 minutes, at which time second wash is removed from reactor. Wash 1 and 2 are combined and dried down to give 17.55 grams of N-methylglucamine product. The dried product is essentially colorless and can be used in an "R-2" reaction to give colorless R-2 product such as lauroyl N-methylglucamide, as described below.

The polyhydroxyamine products of the aforesaid R-1 reaction, preferably with water substantially removed, are desirable and can be further employed in an amide-forming reaction which is designated herein as the "R-2" reaction. A typical R-2 amide-forming reaction herein can be illustrated by the formation of lauroyl N-methyl glucamide, as follows.

$R^2$COOMe + MeN(H)CH$_2$(CHOH)$_4$CH$_2$OH 

$R^2$C(O)N(Me)CH$_2$(CHOH)$_4$CH$_2$OH + MeOH wherein $R^2$ is $C_{11}H_{23}$ alkyl.

Thus, the invention herein encompasses an overall process for preparing polyhydroxy fatty acid amide surfactants, all as noted above for the R-1 process, comprising:

(a) reacting a reducing sugar or reducing sugar derivative with an amine in an organic hydroxy solvent (preferably, methanol) to provide an adduct;

(b) reacting said adduct from step (a) (preferably, as noted above, free from interfering amounts of unreacted amine starting material) dissolved in said solvent (preferably, methanol) with hydrogen in the presence of a catalyst;

(c) removing said catalyst and substantially removing water from the reaction mixture to provide the polyhydroxyamine reaction product; and, thereafter, per the R-2 process, (d) reacting said substantially anhydrous polyhydroxyamine product from step (c) with a fatty acid ester in an organic hydroxy solvent (preferably, methanol) in the presence of a base catalyst to form the polyhydroxy fatty acid amide surfactant (preferably, at a temperature below about 100° C.); and (e) optionally, removing said solvent used in step (d).

More specifically, the combination of R-1 and R-2 reactions herein provides an overall process (R-1 plus R-2) which can be used to prepare polyhydroxy fatty acid amide surfactants of the formula:

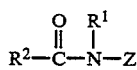  (I)

wherein: $R^1$ is H, $C_1$-$C_4$ hydrocarbyl, 2-hydroxyethyl, 2-hydroxy propyl, or a mixture thereof, preferably $C_1$-$C_4$ alkyl, more preferably $C_1$ or $C_2$ alkyl, most preferably $C_1$ alkyl (i.e., methyl); and $R^2$ is a $C_5$-$C_{31}$ hydrocarbyl moiety, preferably straight chain $C_7$-$C_{19}$ alkyl or alkenyl, more preferably straight chain $C_9$-$C_{17}$ alkyl or alkenyl, most preferably straight chain $C_{11}$-$C_{17}$ alkyl or alkenyl, or mixture thereof; and Z is a polyhydroxyhydrocarbyl moiety having a linear hydrocarbyl chain with at least 3 hydroxyls directly connected to the chain, or an alkoxylated derivative (preferably ethoxylated or propoxylated) thereof. Z preferably will be derived from a reducing sugar in a reductive amination reaction; more preferably Z is a glycityl moiety. Suitable reducing sugars include glucose, fructose, realrose, lactose, galactose, mannose, and xylose. As raw materials, high dextrose corn syrup, high fructose corn syrup, and high realrose corn syrup can be utilized as well as the individual sugars listed above. These corn syrups may yield a mix of sugar components for Z. It should be understood that it is by no means intended to exclude other suitable raw materials. Z preferably will be selected from the group consisting of —$CH_2$—$(CHOH)_n$—$CH_2OH$, —$CH(CH_2OH)$—$(CHOH)_{n-1}$—$CH_2OH$, —$CH_2$—$(CHOH)_2(CHOR')(CHOH)$—$CH_2OH$, where n is an integer from 3 to 5, inclusive, and R' is H or a cyclic mono- or poly- saccharide, and alkoxylated derivatives thereof. Most preferred are glycityls wherein n is 4, particularly —$CH_2$—$(CHOH)_4$—$CH_2OH$.

In Formula (I), $R^1$ can be, for example, N-methyl, N-ethyl, N-propyl, N-isopropyl, N-butyl, N-isobutyl, N-2-hydroxy ethyl, or N-2-hydroxy propyl.

$R^2$—CO—N< can be, for example, cocamide, stearamide, oleamide, lauramide, myristamide, capricamide, palmitamide, tallowamide, etc.

Z can be 1-deoxyglucityl, 2-deoxyfructityl, 1-deoxymaltityl, 1-deoxylactityl, 1-deoxygalactityl, 1-deoxymannityl, 1-deoxymaltotriotityl, etc.

The following reactants, catalysts and solvents can conveniently be used in the R-2 reaction herein, and are listed only by way of exemplification and not by way of limitation. Such materials are all well-known and are routinely available from a variety of commercial sources.

Reactants—Various fatty esters can be used in the R-2 reaction, including mono-, di- and tri-esters (i.e., triglycerides). Methyl esters, ethyl esters, and the like are all quite suitable. The polyhydroxyamine reactants include reactants available from the above-described R-1 reaction, such as N-alkyl and N-hydroxyalkyl polyhydroxyamines with the N-substituent group such as $CH_3$—, $C_2H_5$—, $C_3H_7$—, $HOCH_2CH_2$—, and the like. (Polyhydroxyamines available from the R-1 reaction are preferably not contaminated by the presence of residual amounts of metallo hydrogenation catalysts, although a few parts per million [e.g., 10–20 ppm] can be present.) Mixtures of the ester and mixtures of the polyhydroxyamine reactants can also be used.

Catalysts—The catalysts used in the R-2 reaction are basic materials such as the alkoxides (preferred), hydroxides (less preferred due to possible hydrolysis reactions), carbonates, and the like. Preferred alkoxide catalysts include the alkali metal $C_1$-$C_4$ alkoxides such as sodium methoxide, potassium ethoxide, and the like. The catalysts can be prepared separately from the reaction mixture, or can be generated in situ using an alkali metal such as sodium. For in situ generation, e.g., sodium metal in the methanol solvent, it is preferred that the other reactants not be present until catalyst generation is complete. The catalyst typically is used at a level of about 5 mole % of the ester reactant. Mixtures of catalysts can also be used.

Solvents—The organic hydroxy solvents used in the R-2 reaction include, for example, methanol, ethanol, propanol, iso-propanol, the butanols, glycerol, 1,2-propylene glycol, 1,3-propylene glycol, and the like. Methanol is a preferred alcohol solvent and 1,2-propylene glycol is a preferred diol solvent. Mixtures of solvents can also be used.

General R-2 Reaction Conditions—It is an objective herein to prepare the desired products while minimizing the formation of cyclized by-products, ester amides and color bodies. Reaction temperatures below about 135° C., typically in the range of from about 40° C. to about 100° C., preferably 50° C. to 80° C., are used to achieve this objective, especially in batch processes where reaction times are typically on the order of about 0.5–2 hours, or even up to 6 hours. Somewhat higher temperatures can be tolerated in continuous processes, where residence times can be shorter.

The following examples are intended to illustrate the practice of the R-2 reaction using the N-polyhydroxyamines prepared by the above-disclosed R-1 reaction (with $H_2O$ having been removed), but are not intended to be limiting thereof. It is pointed out that the concentration ranges of the reactants and solvent in Example III provide what can be termed a "70% concentrated" (with respect to reactants) reaction mixture. This 70% concentrated mixture provides excellent results, in that high yields of the desired polyhydroxy fatty acid amide product are secured rapidly. Indeed, indications are that the reaction is substantially complete within one hour, or less. The consistency of the reaction mixture at the 70% concentration level provides ease of handling. However, even better results are secured at the 80% and 90% concentration levels, in that chromotography data indicate that even less of the undesired cyclized by-products are formed at these higher concentrations.

At the higher concentrations the reaction systems are somewhat more difficult to work with, and require more efficient stirring (due to their initial thickness), and the like, at least in the early stages of the reaction. Once the reaction proceeds to any appreciable extent, the viscosity of the reaction system decreases and ease of mixing increases.

EXAMPLE III

A reaction mixture consisting of 84.87 g. fatty acid methyl ester (source: Procter & Gamble methyl ester CE1270), 75 g. N-methyl-D-glucamine (source: Example I, above), 1.04 g. sodium methoxide (source: Aldrich Chemical Company 16,499-2) and 68.51 g. methyl alcohol (30% by wt. of reaction mixture) is used. The reaction vessel comprises a standard reflux set-up fitted with a drying tube, condenser and stir bar. In this procedure, the N-methyl glucamine is combined with methanol with stirring under argon and heating is begun with good mixing (stir bar; reflux). After 15-20 minutes, when the solution has reached the desired temperature, the ester and sodium methoxide catalyst are added. Samples are taken periodically to monitor the course of the reaction, but it is noted that the solution is completely clear by 63.5 minutes. It is judged that the reaction is, in fact, nearly complete at that point. The reaction mixture is maintained at reflux for 4 hours. The recovered reaction mixture weighs 156.16 grams. After vacuum drying, an overall yield of 106.92 grams of granular purified product is recovered, which can easily be ground into smaller particles. However, percentage yields are not calculated on this basis, inasmuch as regular sampling throughout the course of the reaction makes an overall percentage yield value meaningless.

EXAMPLE IV

An overall process at the 80% reactant concentration level for the amide synthesis is as follows.

A reaction mixture consisting of 84.87 g. fatty acid methyl ester (source: Procter & Gamble methyl ester CE1270), 75 g. N-methyl polyhydroxyamine per Example II, above, 1.04 g. sodium methoxide and a total of 39.96 g. methyl alcohol (ca. 20% by wt. of reaction mixture) is used. The reaction vessel comprises a standard reflux set-up fitted with a drying tube, condenser and mechanical stirring blade. The N-methyl glucamine/methanol is heated with stirring under argon (reflux). After the solution has reached the desired temperature, the ester and sodium methoxide catalyst are added. The reaction mixture is maintained at reflux for 6 hours. The reaction is essentially complete in 1.5 hours. After removal of the methanol, the recovered product weighs 105.57 grams. Chromatography indicates the presence of only traces of undesired ester-amide by-products, and no detectable cyclized by-product.

EXAMPLE V

The process of Example IV is repeated at the 90% reactant level for the polyhydroxy fatty acid amide synthesis step. Levels of undesirable by-products are extremely low, and reaction is essentially complete at 30 minutes. In an alternate mode, the reaction can be initiated at a 70% reactant concentration. methanol can be stripped during the course of the reaction and the reaction taken to completion.

EXAMPLE VI

The process of Example III is repeated in ethanol (99%) and 1,2-propylene glycol (essentially dry), respectively, with good product formation. In an alternate mode, a solvent such as 1,2-propylene glycol is used in the R-2 step, with methanol stripping throughout the process. The resulting surfactant/glycol mix can be used directly in a detergent composition.

While the foregoing disclosure generally relates to a solvent-assisted method for preparing N-methyl polyhydroxy amines, such as N-methyl glucamine, as well as their fatty acid amide derivatives using fatty methyl esters, it is to be understood that variations are available which do not depart from the spirit and scope of this invention. Thus, reducing sugars such as fructose, galactose, mannose, maltose and lactose, as well as sugar sources such as high dextrose corn syrup, high fructose corn syrup and high maltose corn syrup, and the like, can be used to prepare the polyhydroxyamine material (i.e., to replace glucamine) of the reaction. Likewise, a wide variety of fats and oils (triglycerides) can be used herein in place of the fatty esters exemplified above. For example, fats and oils such as soybean oil, cottonseed oil, sunflower oil, tallow, lard, safflower oil, corn oil, canola oil, peanut oil, fish oil, rapeseed oil, and the like, or hardened (hydrogenated) forms thereof, can be used as the source of triglyceride esters for use in the present process. It will be appreciated that the manufacture of detersive surfactants from such renewable resources is an important advantage of the present process. The present process is particularly useful when preparing the longer-chain (e.g., $C_{18}$) and unsaturated fatty acid polyhydroxy amides, since the relatively mild reaction temperatures and conditions herein afford the desired products with minimal by-product formation. A preformed portion of the polyhydroxy fatty acid amide surfactant can be used to assist initiation of the R-2 amide-forming reaction when triglycerides or the longer-chain methyl esters are used as reactants. It has further been determined that surfactant yields in the R-2 process can be increased by simply storing the solidified product (which contains some minor amount of entrained solvent and reactants) e.g., at 50° C., for a few hours after removal from the reaction vessel. Storage in this manner apparently allows the last fraction of unreacted starting materials to continue to form the desired polyhydroxy fatty acid amide surfactant. Thus, yields can be increased appreciably, which is an important consideration in large-scale industrial processes.

The following illustrates the use of the above-described surfactant products of the overall R-1 plus R-2 process to prepare fully-formulated detergent compositions. The examples are not intended to be limiting, since a wide variety of surfactants, builders and optional detersive adjuncts and other ingredients well-known to detergent formulators can be used in such compositions, all at conventional usage levels.

EXAMPLE VII

A typical powdered laundry detergent composition is prepared using standard procedures, as follows.

| Ingredient | Percent (wt.) |
| --- | --- |
| Coconut N-methylglucamide* | 8.0 |
| $C_{12}$-$C_{14}$ alkyl benzene sulfonate, Na salt | 9.0 |
| Sodium sulfate | 10.0 |

-continued

| Ingredient | Percent (wt.) |
|---|---|
| Zeolite A (1-10 micron size) | 30.0 |
| Sodium carbonate | 30.0 |
| Brightener | 1.0 |
| Optional perfumes and minors | 3.0 |
| Residual moisture | Balance |

*Prepared in 1,2 propylene glycol, with methanol stripping per Example VI; resulting mix of surfactant/glycol is added to the detergent composition; fatty acids derived from $C_{12}$-$C_{14}$ coconut oil.

EXAMPLE VIII

A typical liquid laundry detergent composition is as follows.

| Ingredient | Percent (wt.) |
|---|---|
| Coconut N-methylglucamide* | 15.0 |
| $C_{12}$-$C_{14}$ fatty acid | 3.0 |
| Citric acid | 3.0 |
| Monoethanolamine | 2.5 |
| Ethanol | 3.5 |
| $C_{14-15}$ alkyl ethoxylate (7.5 avg. EO) | 10.0 |
| Sodium $C_{12-14}$ alkyl sulfate | 7.0 |
| Water | Balance |

*Prepared as 90% R-2 reaction mixture in ethanol; entire mix is added to the detergent composition; fatty acids derived from $C_{12}$-$C_{16}$ coconut oil.

As can be seen from the latter two examples hereinabove, the present invention also encompasses a process for preparing a fully-formulated laundry detergent composition, or the like, comprising admixing the solvent-containing reaction product of the polyhydroxy fatty acid amide-forming R-2 reaction with otherwise conventional detersive surfactants and detersive adjuncts.

What is claimed is:

1. A process carried out under non-oxidizing conditions for preparing N-methyl glucamine, comprising the steps of:
   a) reacting glucose with N-methyl amine at a mole ratio of about 1:1 amine:sugar in methanol or 1,2-propylene glycol solvent at a temperature in the range of from about 30° C. to about 60° C. for a period from about 1-10 hours and removing unreacted amine to provide an adduct;
   b) reacting said substantially amine-free adduct from step (a) with hydrogen at a temperature from about 40° C. to about 120° C. said adduct being dissolved in methanol or 1,2-propylene glycol solvent, in the presence of a nickel catalyst; and
   c) removing said catalyst and substantially removing the water and solvent from the reaction mixture to secure the N-methyl glucamine.

* * * * *